(12) United States Patent
Da Ros et al.

(10) Patent No.: US 9,827,408 B2
(45) Date of Patent: Nov. 28, 2017

(54) DEVICE FOR INSERTING NEEDLES

(71) Applicant: DEBIOTECH S.A., Lausanne (CH)

(72) Inventors: Jérôme Da Ros, Thonon les Bains (FR); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 278 days.

(21) Appl. No.: 14/400,247

(22) PCT Filed: May 8, 2013

(86) PCT No.: PCT/IB2013/053708
§ 371 (c)(1),
(2) Date: Nov. 10, 2014

(87) PCT Pub. No.: WO2013/168107
PCT Pub. Date: Nov. 14, 2013

(65) Prior Publication Data
US 2015/0141954 A1    May 21, 2015

(30) Foreign Application Priority Data
May 10, 2012 (EP) .................................. 12167545

(51) Int. Cl.
*A61M 5/20* (2006.01)
*A61M 37/00* (2006.01)
(Continued)

(52) U.S. Cl.
CPC .......... *A61M 37/0015* (2013.01); *A61M 5/20* (2013.01); *A61M 5/2033* (2013.01);
(Continued)

(58) Field of Classification Search
CPC ...... A61M 37/0015; A61M 2037/0023; A61M 5/46; A61M 2005/1585; A61M 5/2033; A61M 2005/2073
See application file for complete search history.

(56) References Cited

U.S. PATENT DOCUMENTS 4,886,499 A * 12/1989 Cirelli ................... A61M 5/142
128/DIG. 12
6,743,211 B1 * 6/2004 Prausnitz ........... A61B 5/14514
424/449
(Continued)

FOREIGN PATENT DOCUMENTS

JP        2002-728 A       1/2002
WO   2004/019777 A2    3/2004
(Continued)

OTHER PUBLICATIONS

International Search Report for PCT/IB2013/053708, dated Sep. 4, 2013.
(Continued)

*Primary Examiner* — Aarti B Berdichevsky
(74) *Attorney, Agent, or Firm* — Nixon & Vanderhye P.C.

(57) ABSTRACT

A device for inserting at least one hollow needle for the injection or withdrawal of a solution into/from a tissue, said device comprising a casing (1), a plunger (2) movably mounted inside the casing, and propulsion means (3 and 4) suitable for driving the plunger towards the distal end (1*a*) of the device by applying a force F1(*t*). The propulsion means and/or the plunger comprise retaining means (3*a*) for joining the propulsion means and the plunger while the latter is moving, said retaining means releasing the plunger from the propulsion means when a force F2(*t*) is exerted in the opposite direction to F1(*t*). Pressure means hold the needle in the tissue and allow a controlled withdrawal of the plunger at least while the solution is being injected.

16 Claims, 22 Drawing Sheets

Figure 1A:
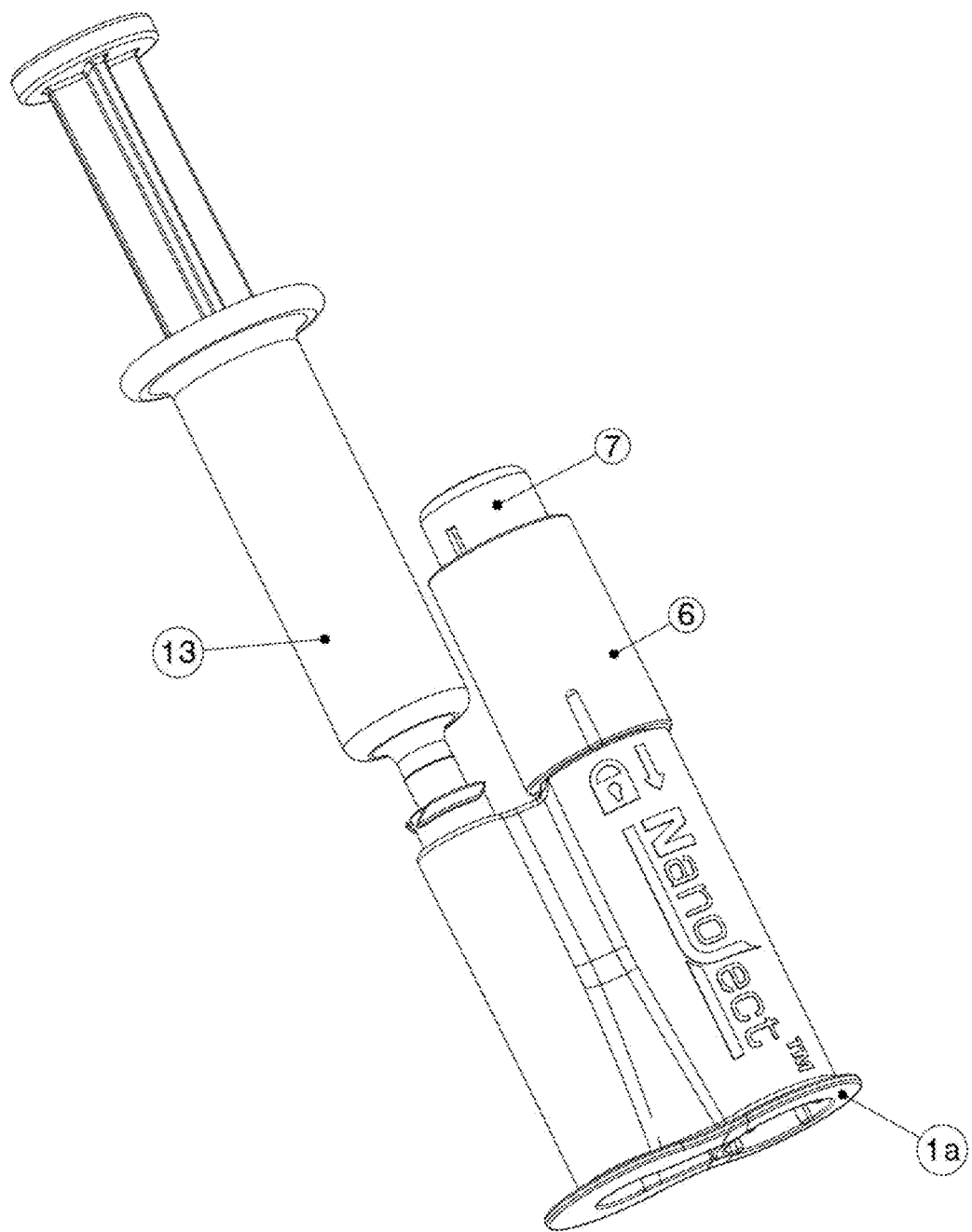

(51) Int. Cl.
*A61M 5/32* (2006.01)
*A61M 5/46* (2006.01)

(52) U.S. Cl.
CPC ............ *A61M 5/3287* (2013.01); *A61M 5/46* (2013.01); *A61M 2005/206* (2013.01); *A61M 2005/2073* (2013.01); *A61M 2037/0023* (2013.01); *A61M 2037/0061* (2013.01)

(56) References Cited

U.S. PATENT DOCUMENTS

| | | | | |
|---|---|---|---|---|
| 7,083,592 | B2* | 8/2006 | Lastovich | A61M 5/14244 604/47 |
| 9,402,984 | B2* | 8/2016 | Lemaire | A61M 5/158 |
| 2008/0183144 | A1* | 7/2008 | Trautman | A61M 37/0015 604/272 |
| 2010/0030148 | A1* | 2/2010 | Alchas | A61M 5/14244 604/115 |
| 2010/0121307 | A1 | 5/2010 | Lockard et al. | |
| 2011/0276027 | A1 | 11/2011 | Trautman et al. | |

FOREIGN PATENT DOCUMENTS

| | | |
|---|---|---|
| WO | WO 2004/019777 | 3/2004 |
| WO | 2005/049107 A2 | 6/2005 |
| WO | WO 2005/049107 | 6/2005 |
| WO | 2008/020780 A1 | 2/2008 |
| WO | WO 2008/020780 | 2/2008 |
| WO | 2012/046816 A1 | 4/2012 |
| WO | WO 2012/046816 | 4/2012 |

OTHER PUBLICATIONS

Foreign-language Written Opinion for PCT/IB2013/053708, dated Sep. 4, 2013.
European Search Report dated Oct. 19, 2012, issued in European Patent Application No. 12167545.
Written Opinion dated Oct. 19, 2012, issued in European Patent Application No. 12167545.8.
Patent Examination Report No. 1 dated Oct. 26, 2016, issued in Australian Patent Application No. 2013257641.
The First Office Action dated Mar. 31, 2016, issued in Chinese Patent Application No. 2013800244067 and English translation.
The Second Office Action dated Nov. 24, 2016, issued in Chinese Patent Application No. 2013800244067 and English translation.
Notice of Reasons for Rejection dated Jan. 4, 2017, issued in Japanese Patent Application No. 2015-510928 and English translation.

* cited by examiner

DEVICE FOR INSERTING NEEDLES

This application is a National Phase of International Application No. PCT/IB2013/053708, filed on May 8, 2013, which designated the U.S., and claims priority to EP Application No. 12167545.8, filed on May 10, 2012, the entire contents of each of which are hereby incorporated by reference.

FIELD OF THE INVENTION

The present invention relates to the insertion of needles, in particular of microneedles. It can be used for intradermal or subcutaneous injection of solutions.

BACKGROUND ART

Devices for inserting microneedles are disclosed in the following documents: U.S. Pat. No. 6,743,211, U.S. Pat. No. 4,886,499, U.S. Pat. No. 7,083,592 and US 20100030148.

LINK WITH THE PRIOR ART

The applications PCT/IB2011/055256 and EP 10193557.5 are incorporated by reference in the present description. Thus, the present application incorporates all the features of, and makes substantial improvements to, the device previously described in said earlier applications.

The present application claims the priority of EP 12167545.8, filed May 10, 2012 in the name of Debiotech SA, the entire content of which document must be considered as forming part of the present application.

GENERAL DESCRIPTION OF THE INVENTION

The present invention is described and characterized by the one or more independent claims, while the dependent claims describe other features of the invention.

In the context of the present invention, the expression "distal end" designates the end farthest away from the operator's hand, and the expression "proximal end" designates the end closest to the operator's hand.

In the context of the present invention, the expression "pressure means" designates at least one element or a combination of elements having the ability to exert a force or to apply a pressure on itself (or themselves) and/or on another element (or another combination of elements). This may involve, without limitation, the attraction or repulsion between two or more elements (for example magnetic elements, the effect of the force of gravity on an element of the device) and/or a mechanical reaction (spring, elastic blade, shape of the element, shape-memory materials) and/or another reaction (chemical reaction, release of a compressed gas).

In the context of the present invention, the term "tissue" designates a collection of cells which in common fulfill a number of functions.

The present invention constitutes an improvement on the methods and devices of the prior art. It relates to a device and a method such as are defined in the claims.

In one possible embodiment, the device comprises a casing, defined by a distal end, which is intended to come into contact with a tissue, and an opposite proximal end, in which a plunger is mounted slidably and can be restricted to a movement in an axis forming the main orientation. At least one hollow needle protrudes from said plunger in order to penetrate said tissue when said plunger is close to or in contact with the tissue. Said plunger is set in motion by thrust means that exert a force $F1(t)$ against said plunger.

The invention makes it possible in particular to impact a tissue with one or more microneedles at relatively high speeds, typically of the order of 3 to 15 m/s (typically 7 m/s), while allowing the tissue to absorb the shock over a certain distance, the effect of which is to improve the perforation of the tissue and to return the latter to a stable state of equilibrium, thereby minimizing the stresses applied to the tissue of the patient. Tissues can have different characteristics depending on their location, age, type of tissue, nature and/or species (animals, plants, humans). Thus, said distance traveled during the shock absorption may be variable or even zero.

The present invention makes it possible in particular to reduce the pressure exerted on the one or more needles (or more generally on the plunger: the latter having the function of supporting the needles) and, consequently, on the tissue during the injection of the solution.

In one embodiment, the microneedles, once inserted, are maintained against the tissue by virtue of a slight pressure possibly different than the thrust means. This slight pressure can prevent the withdrawal of the microneedles at the time of insertion and/or after the insertion and/or during the injection of the fluid. The reason is that, following the impact of the microneedles against the tissue, the tissue is able to exert a counterforce in reaction to said impact; this counterforce can project the plunger in the direction opposite to the direction of insertion and thereby cause said microneedles to retreat from the tissue. Therefore, this slight pressure can have the aim of keeping the microneedles at least partially inserted in the tissue. This slight pressure can also serve to maintain the microneedles in place during the injection in order to prevent any leakage and/or any retreat of the microneedles during the injection. However, this slight pressure must not be able to oppose the formation of papules induced by the injection of the solution, that is to say the slight pressure exerted must permit a slight retreat or movement of the needles with the tissue at the moment of formation of this papule. In particular, this pressure must not compress the tissue too much, i.e. in a way that prevents (or greatly limits) the ability of the fluid to circulate therein. In one embodiment, this slight pressure could allow the device to apply a supplementary force in order to facilitate the insertion of the needles.

In one embodiment, this pressure can be made possible by virtue of pressure means maintaining the needles in place on the tissue once they have penetrated it. However, in order to allow creation of a papule during the injection, these pressure means must not be too great.

In the context of this invention, and in one embodiment and use, intradermal injection can induce the formation of a papule, which corresponds to the deformation of the tissue following the accumulation of the solution injected into the tissue, especially in the case of an injection of the bolus type. It will be noted that it is desirable to create and maintain a papule in order to ensure an optimal injection into the target tissue. It is for this reason that the present invention allows such a papule to form and remain in place for the time needed for good diffusion of the injected substance.

The invention also relates to a method for insertion and injection or withdrawal using one or more needles, especially microneedles, in particular in the dermis, where the needle, provided with a translation movement in a direction corresponding to the main orientation, is able to decelerate suddenly or gradually in the tissue, on account of the elasticity of the latter, along a certain length, while ultimately ensuring that the needle is maintained in place after the insertion and during the injection and/or during the withdrawal, by virtue of a very slight pressure of the needle against the tissue. The needle/plunger assembly can exert a pressure against the tissue during the insertion, in such a way that the needle/plunger assembly can drive into the tissue, where the needle penetrates the tissue and the distal face of the plunger pushes the tissue. The depth of insertion of the needle is ensured by said distal face of the plunger limiting the depth of insertion when the plunger is in contact with the tissue. In one embodiment, the casing comprises a stop that limits the depth of insertion when the plunger is in contact with said stop.

In one embodiment, the device according to the invention also affords the advantage of being able to be used in any orientation with respect to the tissue.

In a preferred embodiment, the plunger and the thrust means are rigidly connected to each other temporarily by retaining means. In one embodiment, the retaining means allow said plunger to be rigidly connected to the thrust means at least for a fraction of the time during which the thrust means are in movement. By way of non-limiting example, the thruster has clips adapted to retain the plunger. Said clips are configured to drive the plunger in the direction of the tissue by virtue of the thruster at the time the insertion is triggered and to unclip once the plunger encounters an oppositely directed force $F2(t)$ above a predetermined level (a non-zero threshold value).

$F1(t)$ and $F2(t)$ are oppositely directed, ideally (but not necessarily) in the same orientation, and at least temporarily not zero. In some embodiments, $F1(t)$ and $F2(t)$ can temporarily be applied to said plunger simultaneously. In another embodiment, the thrust means no longer exert a force but, by virtue of the kinetic energy of the thruster and $F2(t)$ exerted against the plunger, the retaining means free the plunger. Thus, said retaining means disconnect, allowing the thruster to continue its travel (its movement) without applying force or stress to the plunger or doing so only to a limited extent.

In other words, when the device is triggered, the thruster drives the plunger in the direction of the tissue by applying a force $F1(t)$ to it. Once the plunger comes into contact with an element (for example the target tissue, a stop), this element will generate a counterforce (called $F2(t)$) opposite to the direction of insertion, which will be applied to the needle/plunger assembly (also called plunger). $F2(t)$ will grow gradually or instantly as the plunger continues its travel set in motion by the thruster, until it reaches a predetermined value of which the intensity is such that the retaining means are forced to free the plunger (for example by unclipping) from the thrust means.

In one possible embodiment, the thrust means are formed by a thruster that accommodates a spring or an elastic band or an elastic blade.

The retaining means can be configured and arranged depending on the characteristics of the thrust means and on the characteristics of the tissues in which the needles are to be inserted.

In another embodiment, the retaining means disconnect as a result of the impact or by other means such as a limit stop or manually, such that the thruster no longer exerts pressure on the needle/plunger assembly, at least before the start of the injection of the solution.

As has been described above, as a result of the impact of the needles against the tissue and/or of the force $F2(t)$ after release of the retaining means, the needle/plunger assembly can be projected in the direction opposite to that of insertion and can thus cause the partial or complete withdrawal of the needles, even though the latter have initially been correctly inserted. Moreover, during the injection, depending on the characteristics of the microneedles (for example the direction of the one or more channels and/or the shape of the needles described by the patent applications WO 2011/006699, WO 2003/015860, WO 2006/025786, EP 1669100, of which the descriptions are integrally incorporated by reference into the present description), the needles can partially or completely leave their seats. This phenomenon may, for example, be due to the action-reaction principle: the action created by the force of the liquid injected into the tissue generates, by reaction, an oppositely directed force capable of dislodging the needles from the tissue. In order to ensure the correct insertion of the needles and to limit the leakage of the solution to be injected, the pressure means allow the needles to remain inserted in the tissue after the insertion and during the injection.

Thus, in the context of the present invention, at least before the injection, a pressure of the needle/plunger assembly against the tissue is preferably exerted by pressure means. However, for an optimal injection of the solution into or through the tissue, these pressure means must have a sufficiently low force, from the start to the end of the formation of the papule, in order not to limit the formation of this papule during the course of the injection.

To put it another way, said pressure means exert a force $F3(t)$ in a direction corresponding to the main orientation in the direction of insertion (same direction as $F1(t)$), that is to say in the direction of the tissue, without in so doing impeding the formation of the papule.

This force $F3(t)$ can be generated by a single element or several elements which, by way of non-limiting example, can be a tube, a spring, an elastic band, a gas cartridge, compressed air, an electromagnetic force, the generation of gas by chemical reaction between at least two compounds, an elastic blade and/or the weight of the plunger/needle assembly.

In the present document, the frictional forces can be considered to be negligible (or at least very low compared to the other forces at play), and the forces $F1(t)$, $F2(t)$ and $F3(t)$ are at least temporarily not zero. In one embodiment, the threshold value above which the retaining means free the plunger is between 0 and 10 N, ideally between 0.5 and 5 N. The force $F3(t)$ is between 0 and 10 N, ideally less than 5 N.

In one embodiment, the formation of the papule will generate a force $F4(t)$ against the plunger in the same direction as $F2(t)$. In one embodiment, $F4(t)$ is greater than $F3(t)$ and causes a return movement of the plunger in relation to its position before the injection.

In another embodiment, the pressure means exert a force once the thrust means have been activated. The spring of the thrust means can thus couple itself to the pressure means in order to form the source of energy necessary for the thrust means.

In another embodiment, the thrust means are themselves responsible for the residual force at the end of travel. This may correspond, for example, to the end of travel of a spring or of an elastic band used to propel the plunger, said spring or elastic band being calculated in such a way that this residual force at the end of travel corresponds to the required residual force.

In another embodiment, the pressure means can also serve to propel the solution once the microneedles are lodged in the tissue of the patient and the retaining means are released, thereby constituting an auto-injector. In another embodiment, after release of the retaining means, the thrust means permit injection of the solution into the tissue.

The thrust means preferably exert a force in the direction corresponding to the insertion and with a value greater than or equal to the pressure means.

In a preferred embodiment, the device is configured in such a way that any bearing of the device against the tissue does not exert, or only marginally exerts, a pressure on the needle/plunger assembly, such that the formation of the papule cannot be impeded. The distal end of the device is composed of a ring-shaped contact zone and of stabilizer feet making it possible to position the device on the tissue at a desired angle and at a sufficient distance therefrom so as not to influence, or only marginally influence, the mechanical characteristics of the tissue. Moreover, said ring or stabilizer foot has no effect on the depth of insertion of the needles.

In one embodiment, the plunger is initially in a position 0 (or after the priming of the thrust means), in which the needle/plunger assembly is accommodated securely in the casing of the device. The device is configured in such a way that the plunger reaches a first position, after activation of the thrust means, forming a distance D1 between the distal face of the plunger and the proximal end of the casing; then a second position before the injection, forming a distance D2 between the distal face of the plunger and the proximal end of the casing; then a third position, after the injection of at least one solution into or through the tissue, forming a distance D3 between the distal face of the piston and the proximal end of the casing; D3 being less than or equal to D1 and to D2. The pressure means are intended to keep said needle at least partially inserted in the tissue and to allow at least a controlled return movement of the plunger during the transition from the first position to the second position and then to the third position.

The device according to the invention can make it possible to have D1 greater than D2 or, conversely, D1 less than or equal to D2, depending on the characteristics of the tissue and/or on the handling by the operator and/or on the characteristics of the device.

The device preferably has a stop that limits the travel of the plunger. This stop can be positioned in such a way that the plunger can protrude from the distal end of the device. This stop can also permit disconnection of the plunger from the thruster.

In one embodiment, the device has a stop that limits the travel of the thruster, such that the thruster cannot apply pressure to the plunger during the injection.

In one embodiment, the injection can be triggered automatically or manually once the one or more needles are inserted in the tissue, but it will preferably begin once the plunger has returned to the second position, that is to say when the thruster no longer exerts force against the tissue.

In a preferred embodiment, a syringe or a reservoir is fluidically connected to the needles.

The thruster is preferably set in motion by release of a potential energy that can be triggered with the aid of activation means, for example a button or other mechanisms. This energy can be stored in various forms, non-limiting examples being a spring, leaf spring, gas cartridge, compressed air, electromagnetic force, generation of gas by chemical reaction between at least two compounds.

In one possible embodiment, the source of energy can be the operator himself. By pressing with sufficient force, he will generate, via a mechanism within the device, the speed that is necessary for the one or more needles to penetrate the tissue.

The device can also comprise a safety mechanism, making it possible to lock the activation means in order to avoid accidental release. The safety mechanism can take different forms, and the support of the ring or of the device on the tissue can also unlock the detent and permit triggering.

The device can also comprise a receptacle used to store the solution that is to be administered. This receptacle can be positioned on the body of the device or can be directly integrated in the device or can simply be fluidically connected to the needles. The activation of this receptacle, which will cause the injection of the substance into the tissue, can be performed manually or automatically, for example with the aid of the pressure means, the thrust means, weightlessness, or any other elements or mechanisms.

In this second case, once the needles are in place, the activation of the device will cause the activation of the receptacle. This receptacle can take various forms, for example, but not exclusively, a semi-rigid reservoir, a flexible bag, a syringe, a carpule.

In one possible embodiment, before the injection and before the activation of the thrust means, the operator can evacuate the air possibly contained in the fluidic connection or the receptacle. The device can comprise a window at the height of the needle, thus making it possible to see the first drop, proof that the fluidic connection has been emptied of air.

The device can comprise a mechanism or an element making the needle difficult to access, so as to prevent injuries before and/or after the insertion and also after the injection. This protection can be obtained in particular by retracting the needle into the body of the device, or into the support itself, or by sliding or by engaging a cover, or deployment of a protective element which prevents inadvertent access to the needle, at least after the withdrawal of the device from the target tissue. Such a protective system can be automatically triggered once the microneedles have been removed from the tissue of the patient, for example as a result of the residual force.

In one possible embodiment, the needles of the device are microneedles. Microneedles are understood as needles whose dimensions are adapted preferably to the intradermal region. This zone has a variable thickness depending on the patient and depending on the location on the body of one and the same patient. It ranges from several hundred microns to a few millimeters. However, the microneedle may be a little longer than the maximum thickness of this zone in order to take account of the penetration of the microneedles into the tissue, which might only be partial.

The device described in the present document can also permit collection of solution.

LIST OF FIGURES

The invention will be better understood below on the basis of a number of illustrative examples. It goes without saying that the invention is not limited to these embodiments.

FIG. 1: General view of the inserter.
FIG. 2: Exploded view of the inserter and detailed view of the plunger/thruster assembly.
FIG. 3: Sectional view of the inserter with and without spring (4a) used as pressure means.
FIG. 4: Inserter charged and ready to be actuated.
FIG. 5: Inserter in position 1.
FIG. 6: Inserter in position 2.
FIG. 7: Inserter in position 3.

Figure 8:
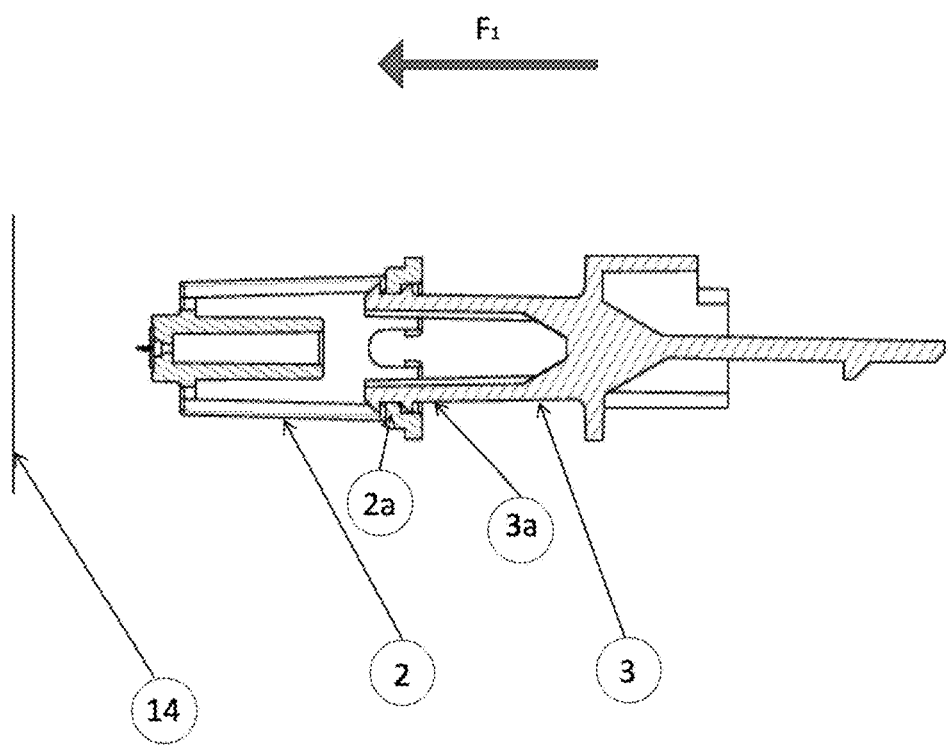

FIG. 8: Release of the plunger/thruster assembly.

Figure 9:
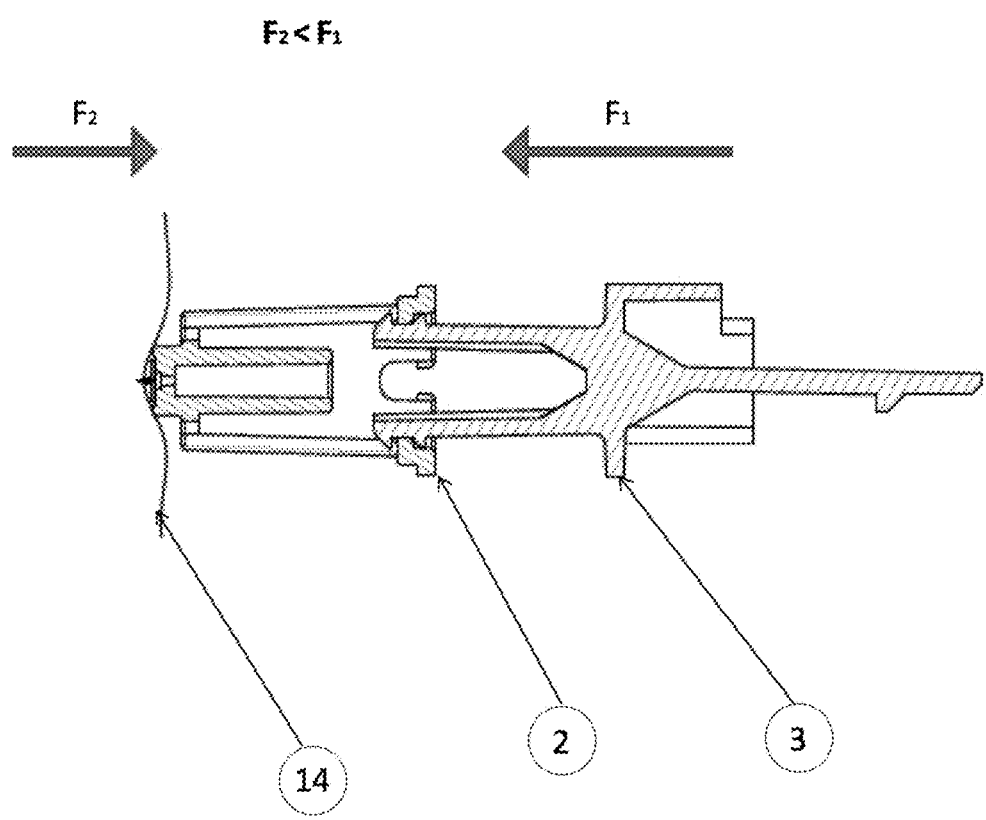

FIG. 9: Start of insertion of the plunger/thruster assembly.

Figure 10:
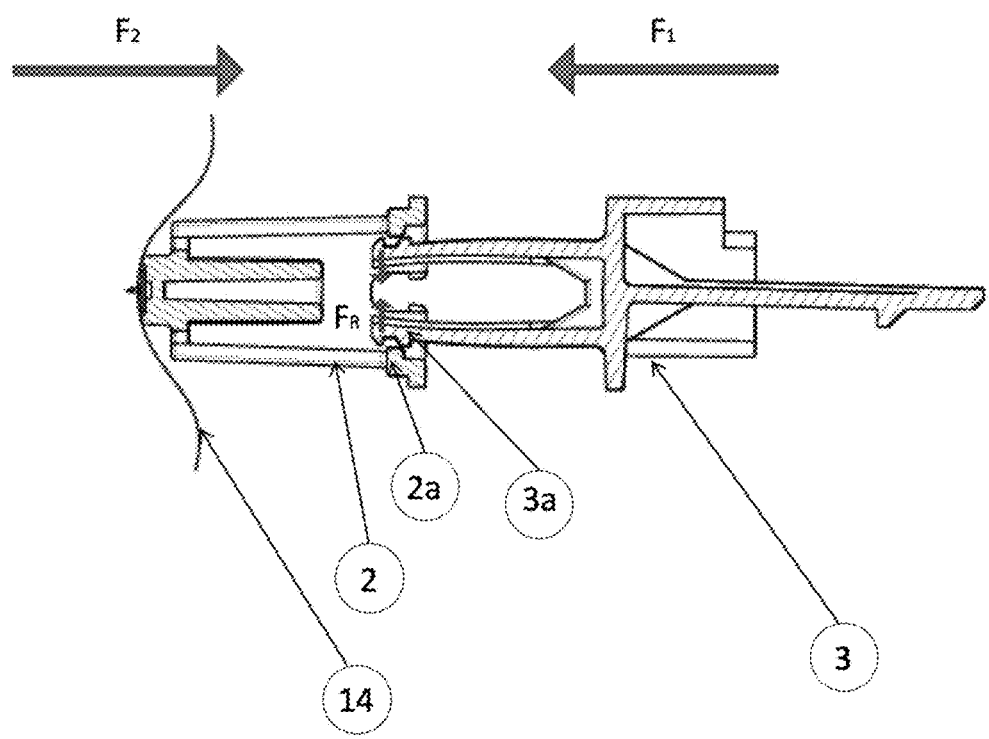

FIG. 10: Plunger/thruster assembly in position 1.

Figure 11:
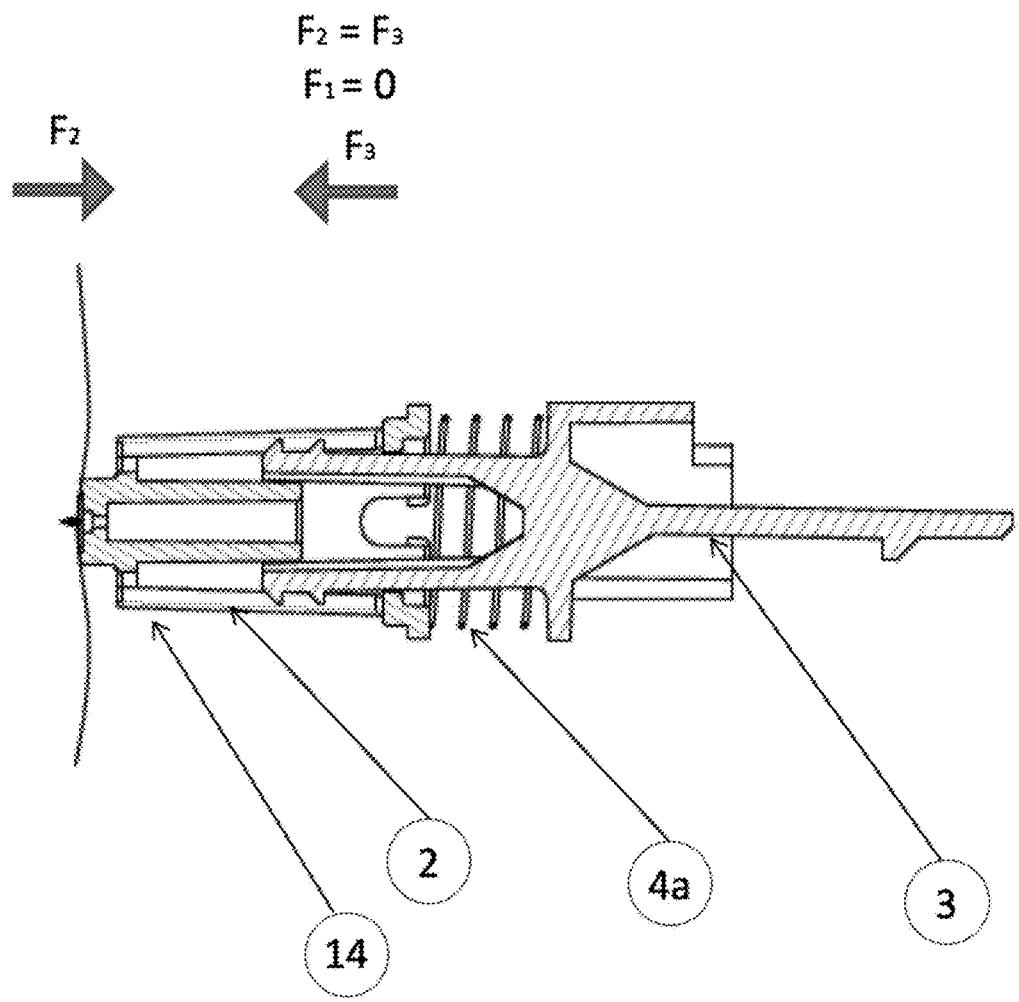

FIG. 11: Plunger/thruster assembly in position 2.

Figure 12:
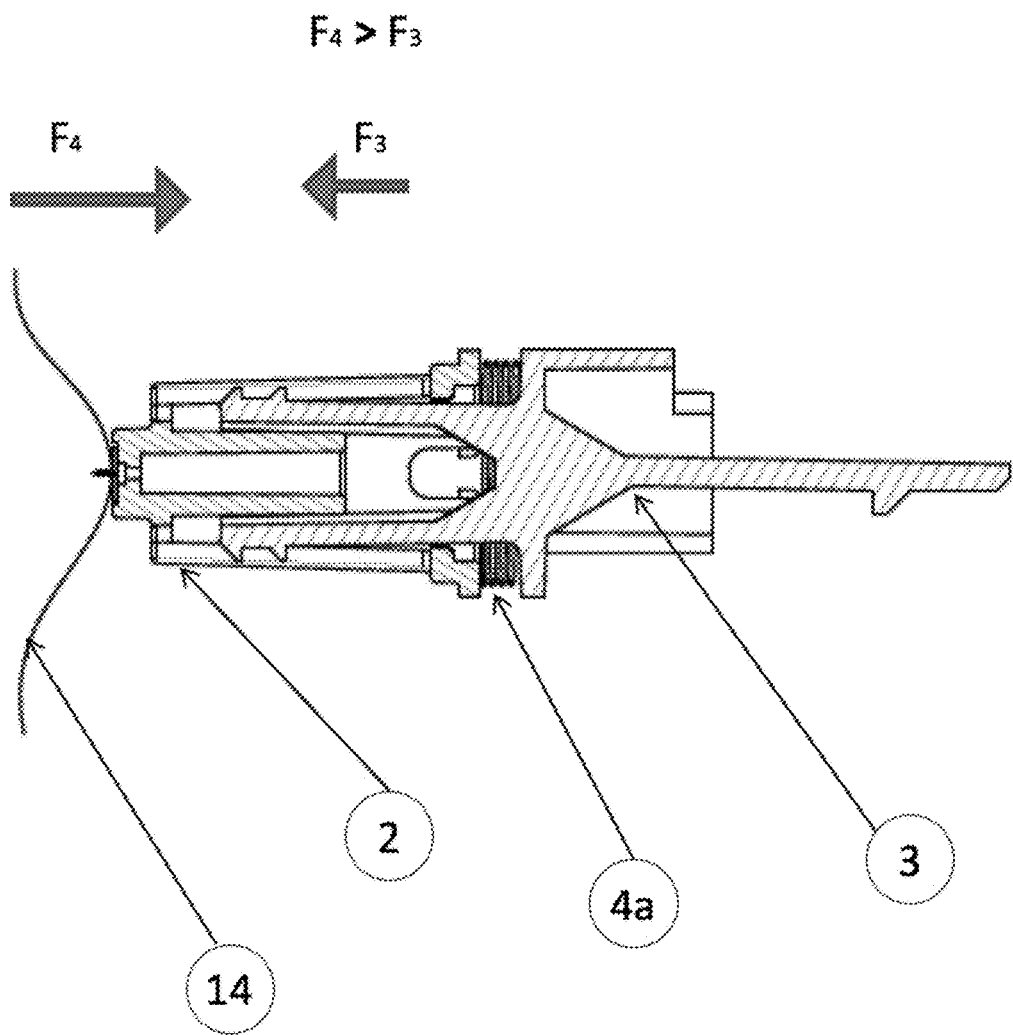

FIG. 12: Plunger/thruster assembly in position 3.

Figure 13:
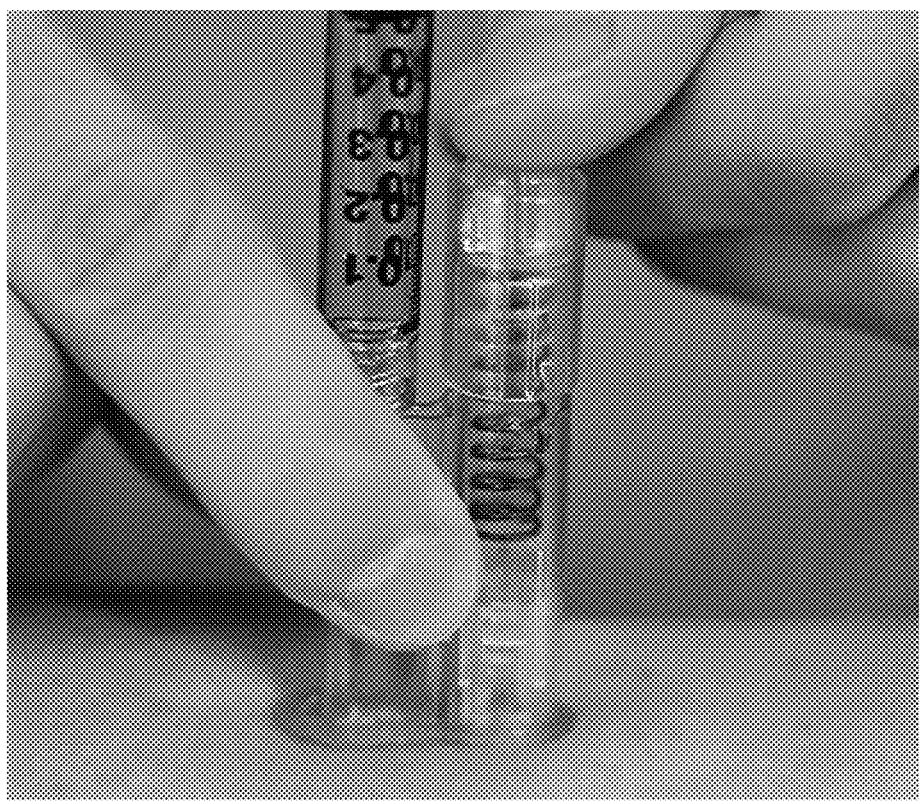

FIG. 13: Inserter after actuation of the thruster.

Figure 14:

FIG. 14: Papule formed after injection of 0.2 ml of solution.

Figure 15:
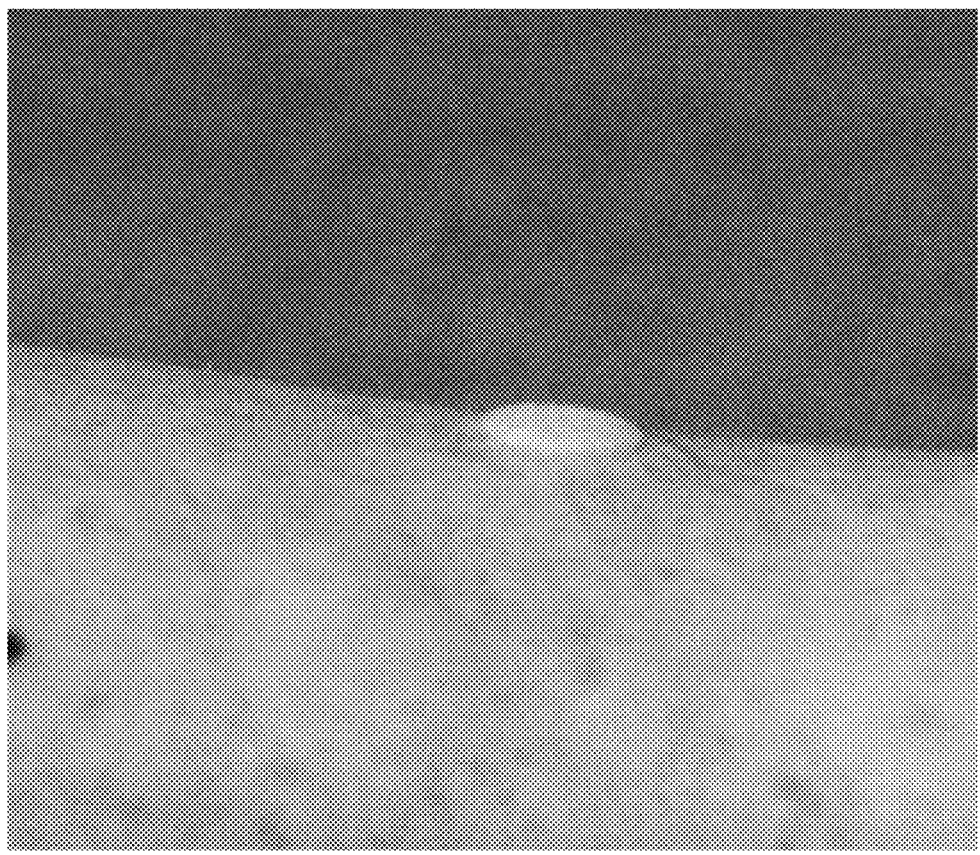

FIG. 15: Papule formed after injection of 0.5 ml of solution.

DETAILED DESCRIPTION OF THE INVENTION

In the present document, the detailed description of the invention includes embodiments of devices, systems and methods that are presented by way of illustration. It will be appreciated that other embodiments are conceivable and may be applied without departing from the scope or spirit of the invention. Therefore, the detailed description given below must not be taken in a restrictive sense.

Unless otherwise indicated, the scientific and technical terms used in the present document have meanings currently used by a person skilled in the art. The definitions given in this document are mentioned in order to facilitate an understanding of the terms frequently used and are not intended to limit the scope of the invention.

The indications of direction used in the description and in the claims, such as "up", "down", "left", "right", "upper", "lower", and other directions or orientations are mentioned in order to afford greater clarity with reference to the figures. These indications are not intended to limit the scope of the invention.

In the present document, the verbs "have", "comprise", "include" or equivalent are used in a broad sense, generally signifying "including but not limited to".

Figure 1B:
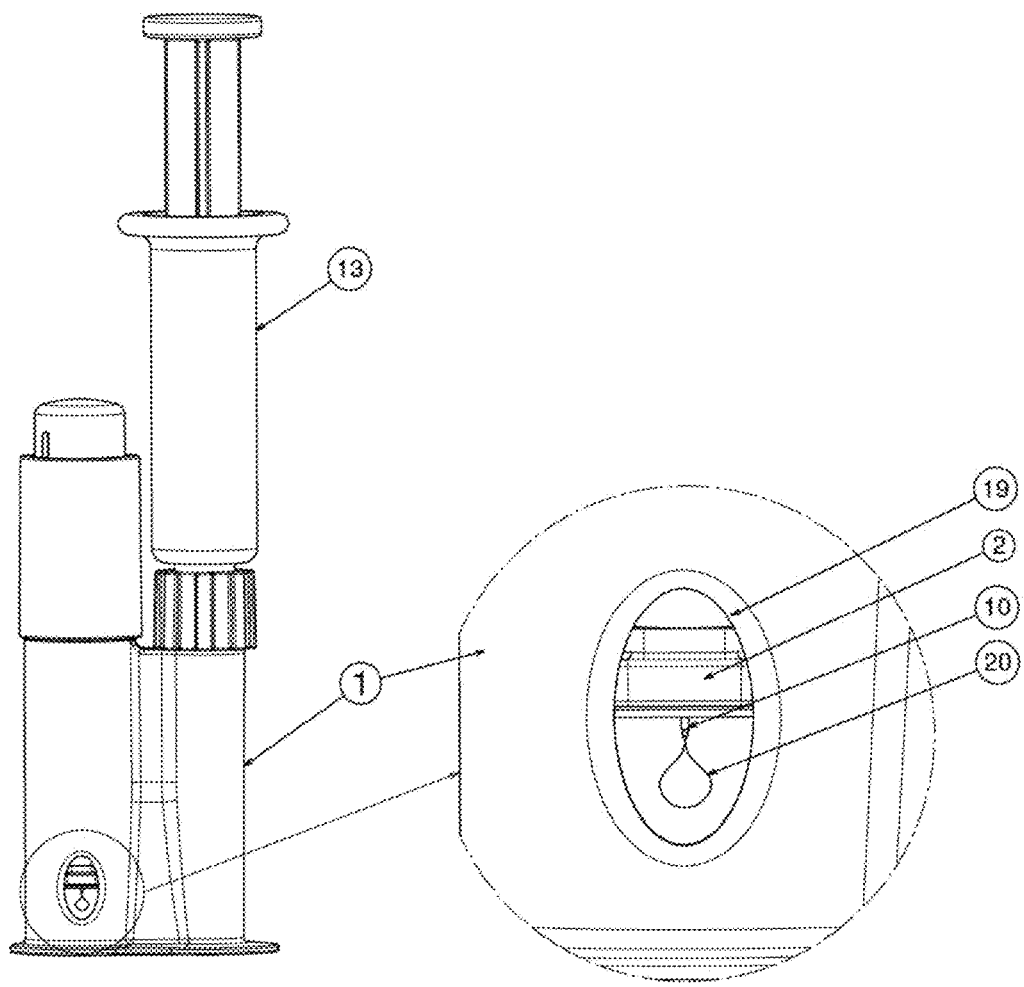

FIGS. 1a and 1b show the various components of the complete device seen from the outside prior to insertion: the casing (1), the distal face (1a) of the device, the trigger (7), and the safety element (6) of the trigger.

In order to evacuate air from the fluidic connection between the syringe (13) and the needle (10) prior to the injection, the device has a window (19) to make it possible to see the needle (10) and to see the first drop (20) of the solution before carrying out the insertion.

Figure 2A:
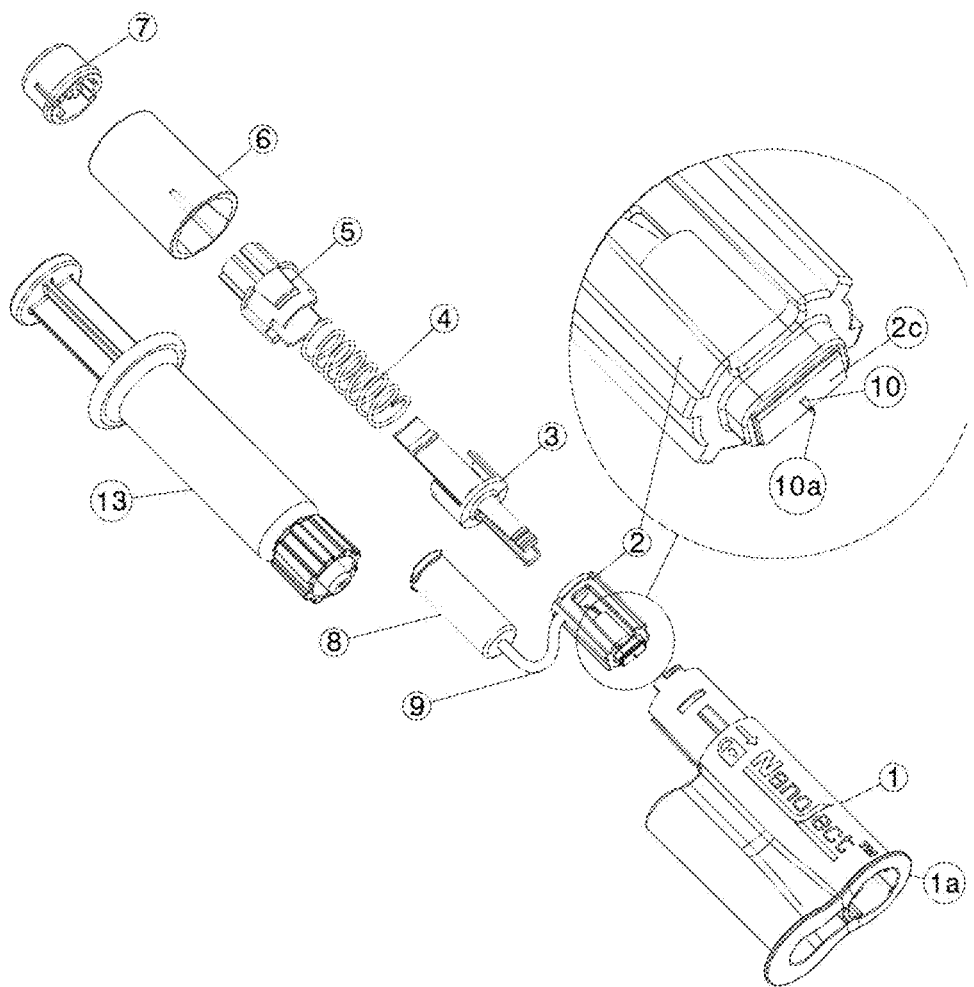

FIG. 2a is an exploded view of the device and reveals the various elements present on the inside:

The Luer (8), which permits connection to the syringe (13), is in fluidic communication with the needle (10) by way of the tube (9).

The thrust means are formed by a spring (4), which is the main source of energy for the insertion and which is compressed between an element (5), rigidly connected to the casing, and the thruster (3), mounted movably in the casing. Such an arrangement ensures a movement guided by the inner wall of the casing in a direction corresponding to the main orientation (16 shown in FIG. 4).

The needle (10) is rigidly connected to the plunger (2) and protrudes from the distal face (2c) of the plunger. The needle (10) itself has a pointed distal end (10a). The size of the needle depends on the characteristics of the tissue in which the injection is to be performed. The distance between the distal face (10a) of the needle and that (2c) of the plunger represents the depth to which the injection is to be performed. The size of the distal face (2c) makes it possible to guarantee this maximum depth.

Figure 2B:
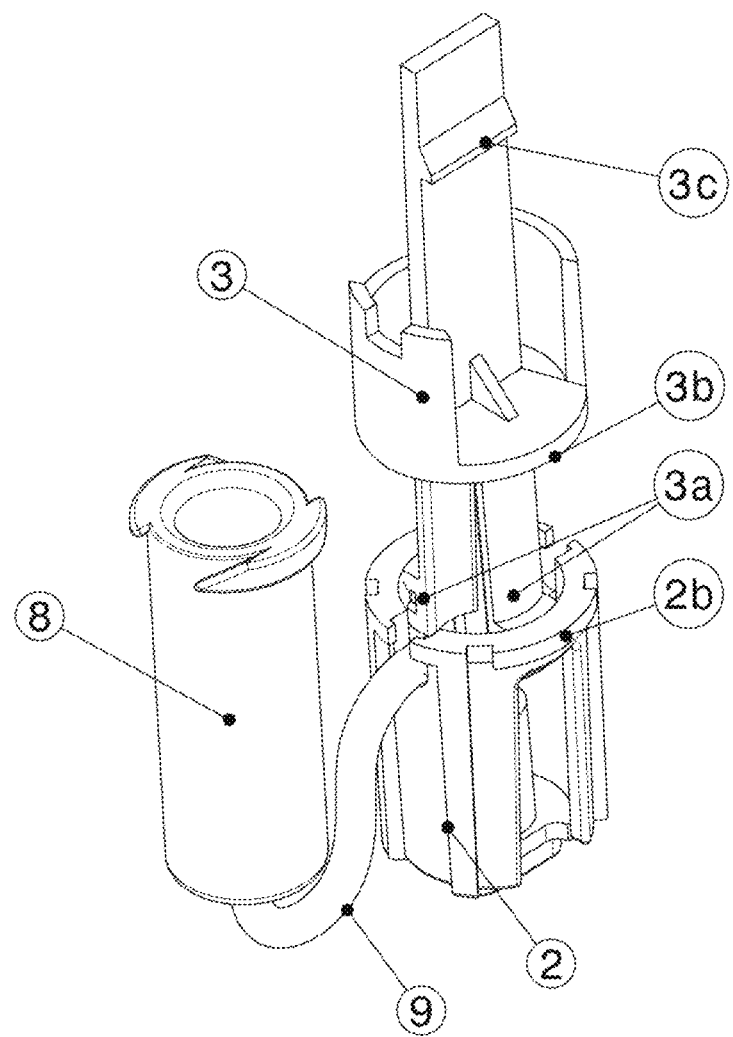

FIG. 2b shows the plunger/thruster assembly (2, 3). The thruster has retaining means (3a) by which this plunger/thruster assembly (2, 3) can temporarily be joined together. The plunger is configured in such a way as to receive the retaining means (3a) by way of the receiving elements (2a shown in FIG. 3a). Figure shows more clearly how the plunger is rigidly connected to the thruster. The retaining means (3a) have two beveled extrusions (per retaining means) in order to clip the plunger (2) to the thruster (3) at the time of assembly and to unclip them prior to the injection.

Figure 3A:
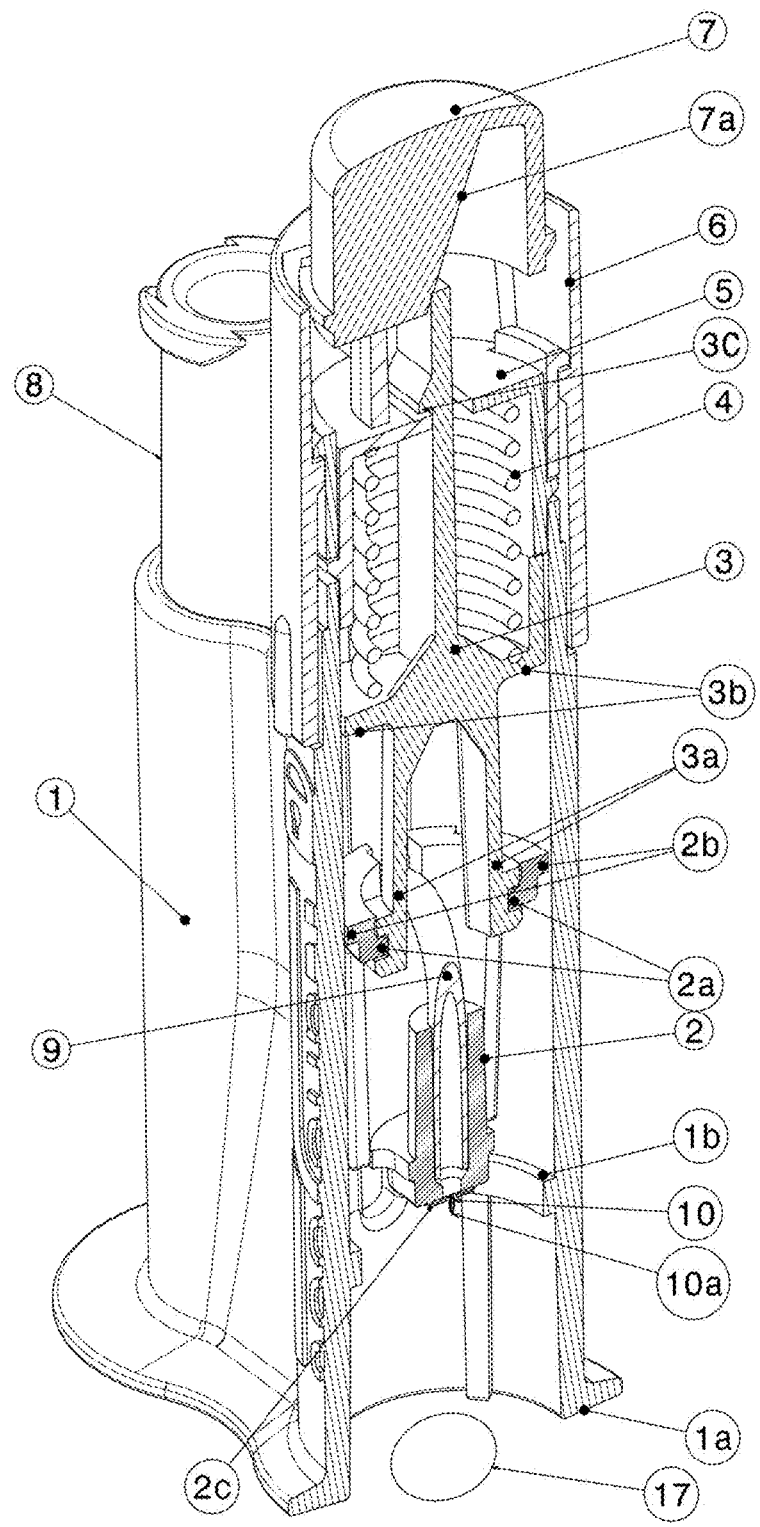
Figure 3B:
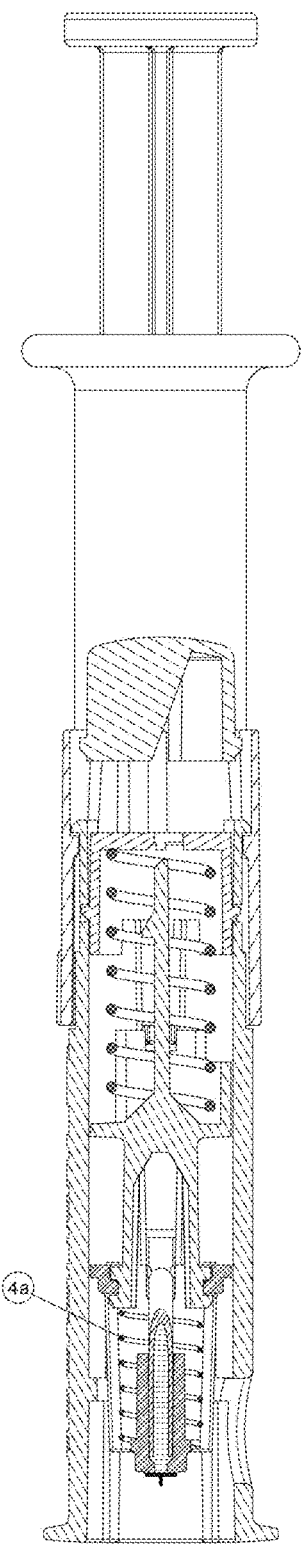

FIGS. 3a and 3b show the inserter when charged, that is to say having the spring (4) compressed and ready to carry out the insertion. FIG. 3b differs from FIG. 3a only in terms of the presence of the spring (4a), which acts as pressure means.

According to FIG. 3a, the needle (10) is rigidly fixed to the plunger (2), which is itself rigidly connected to the thruster (3). The spring (4) is compressed between the thruster (3) and an element (5) rigidly connected to the casing. This position, called "device charged", is maintained temporarily by the retaining element (3c) to the element (5) rigidly connected to the casing. The operator has to unlock the safety element (6) in order to depress the trigger (7), which in turn releases the retaining element (3c).

The casing has guide means (1d) restricting the plunger to a movement in the main direction in order to come into contact at a predefined zone (17). The casing also contains stops (1b) and (1c shown in FIG. 5), which respectively limit the travel of the plunger and of the thruster. The stop (1b) nonetheless allows the distal face (2c) of the plunger to pass beyond the distal end (1a) of the device and is able to force the retaining elements (3c) to unclip if the resistance of the tissue has not permitted this unclipping beforehand. The stop (1c) maintains the thruster (3) such that it no longer exerts pressure via its spring (4) directly on the plunger (2).

FIGS. 4 to 7 disclose the complete device from positioning to injection.

Figures 4A, 4B:
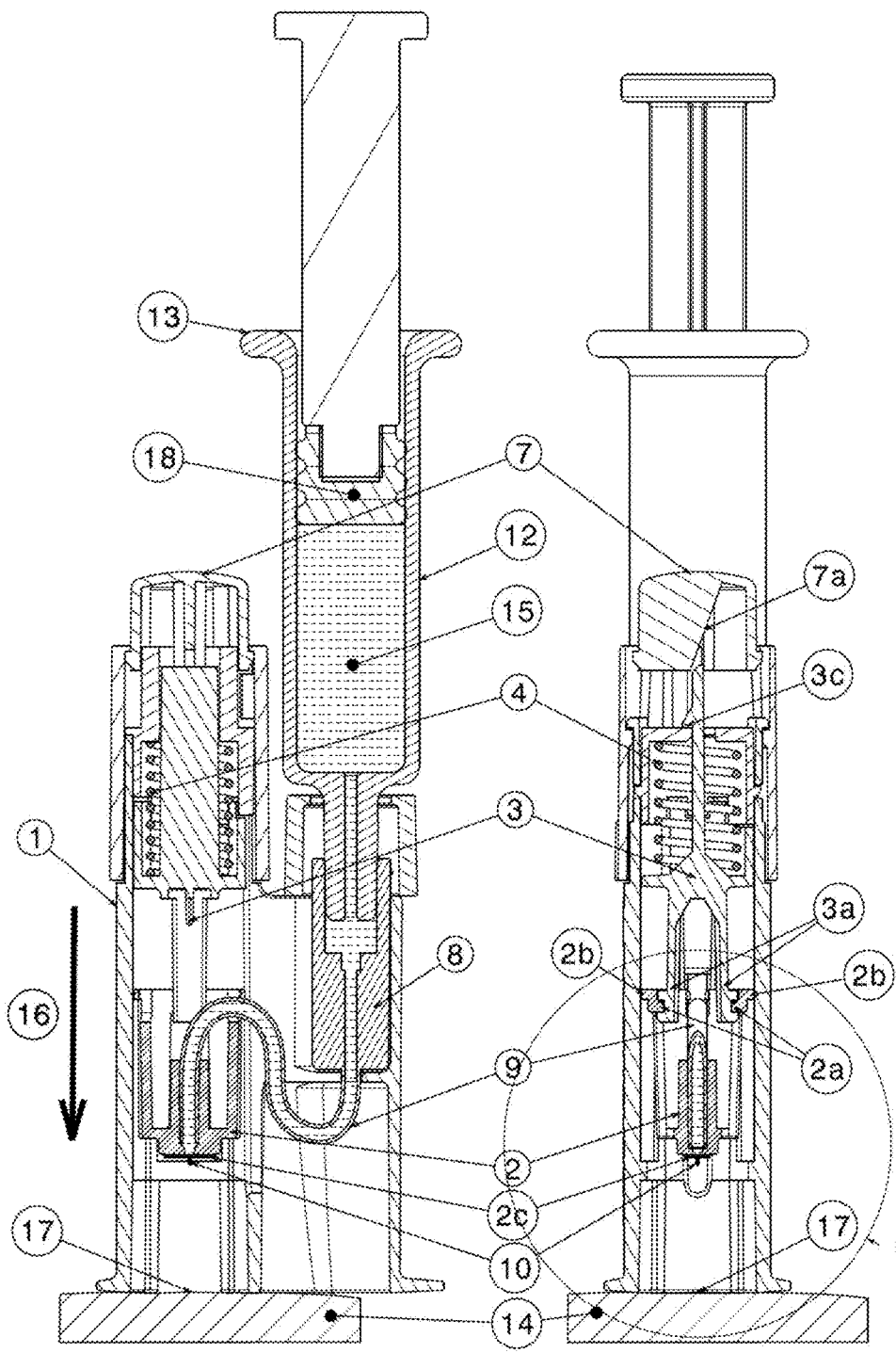
Figure 4C:
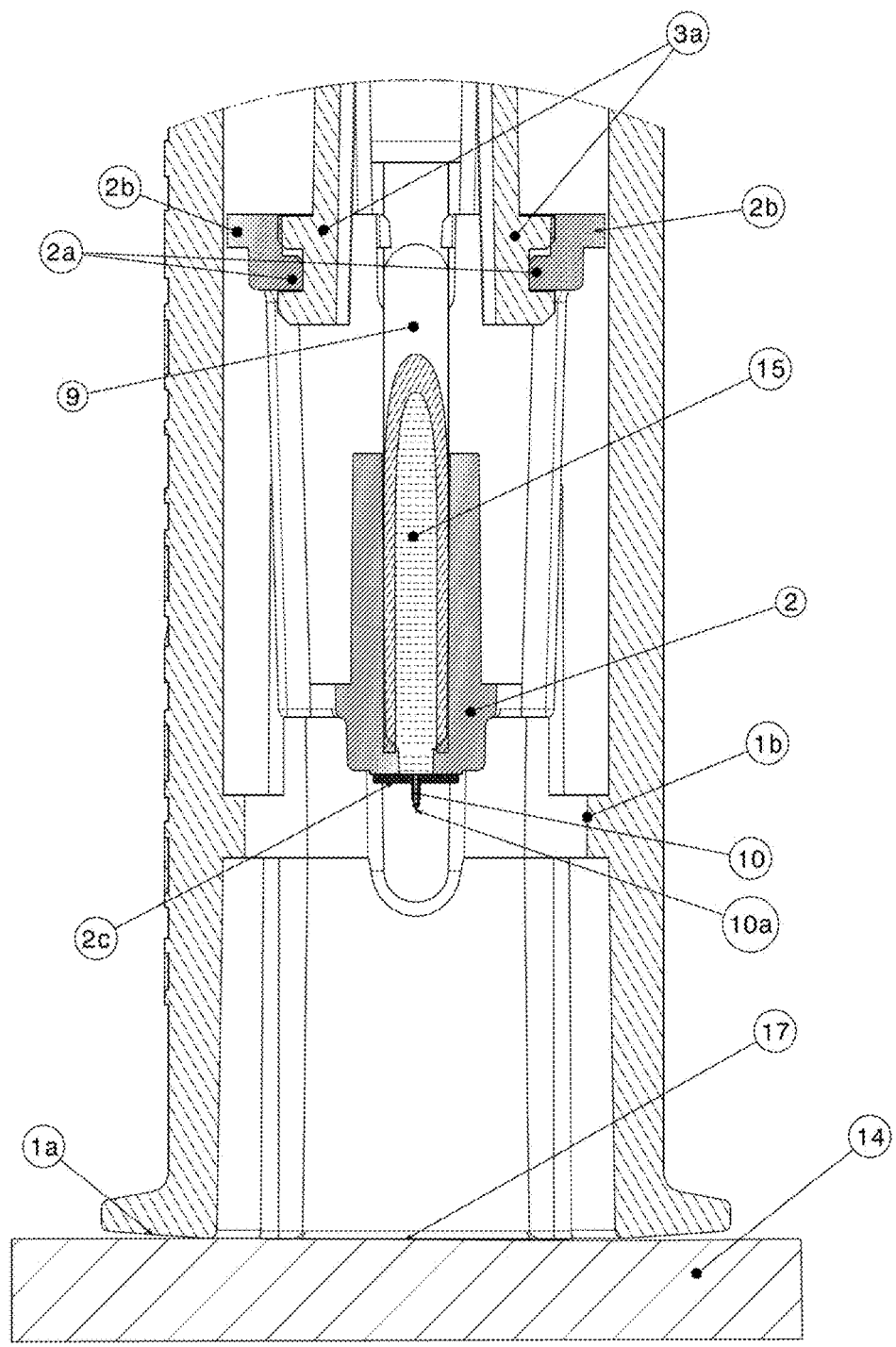

FIGS. 4a, 4b and 4c show the device positioned on the tissue in order to inject the solution beneath the contact zone (17). The plunger/thruster assembly (2, 3) is integrally joined, the spring (4) compressed. At this stage, the operator can exert a slight pressure on the plunger (18) of the syringe in order to evacuate air from the fluidic connection comprising the Luer (8) and the tube (9). A window (19 shown in FIG. 1b) makes it possible to verify when the first drop (20) of the solution (15) leaves the needle (10).

Figures 5A, 5B:
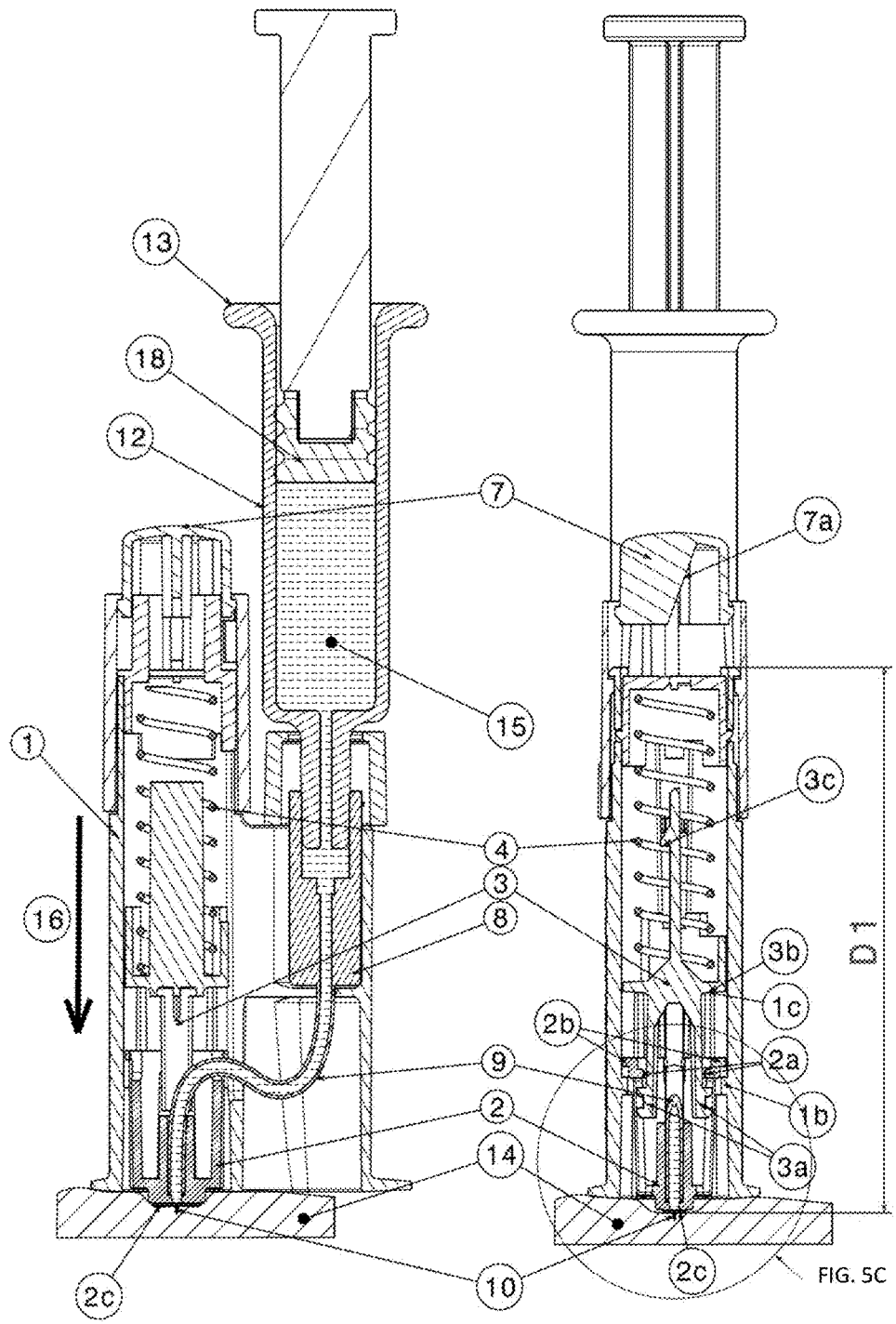
Figure 5C:
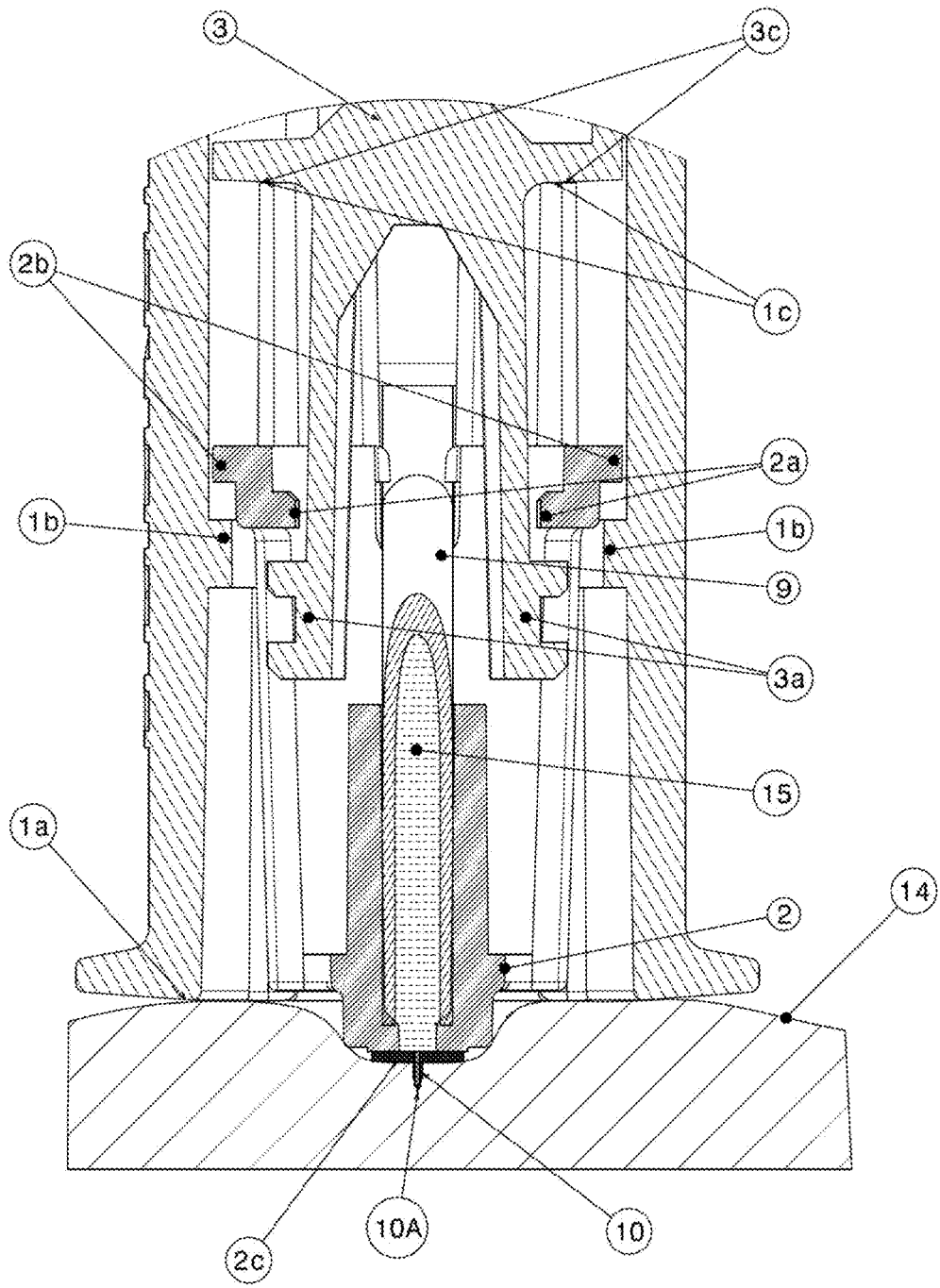

FIGS. 5a, 5b and 5c show the device with the plunger (2) in position 1, thus forming a distance D1 between the proximal end of the casing and the distal face (2a) of the plunger. According to this configuration, the plunger has thus reached its position farthest away from the proximal end of the casing. It is possible, however, for the operator to apply such a pressure to the device that an artificial bead forms. In this case, D1 could not be the maximum distance between the proximal end of the casing and the distal face (2a) of the plunger.

At this stage, the retaining means (3a) can unclip themselves, thereby freeing the plunger (2) of any force exerted directly by the thruster (3). The unclipping may be caused by the elastic resistance of the tissue or by the stop 1b, both exerting a force that opposes the force exerted by the thruster. However, the needle/plunger assembly (10, 2) is constrained by pressure means (for example 4a shown in FIG. 3b) exerting a force in the direction of insertion (16) so as to keep the needle (10) correctly inserted in the tissue (14). It will be noted that the inverted S shape of the tube (9) can also define the pressure means. The pressure means can be active once the device has been activated or at least once the distal face (10a) of the needle touches the tissue (14).

Figures 6A, 6B:
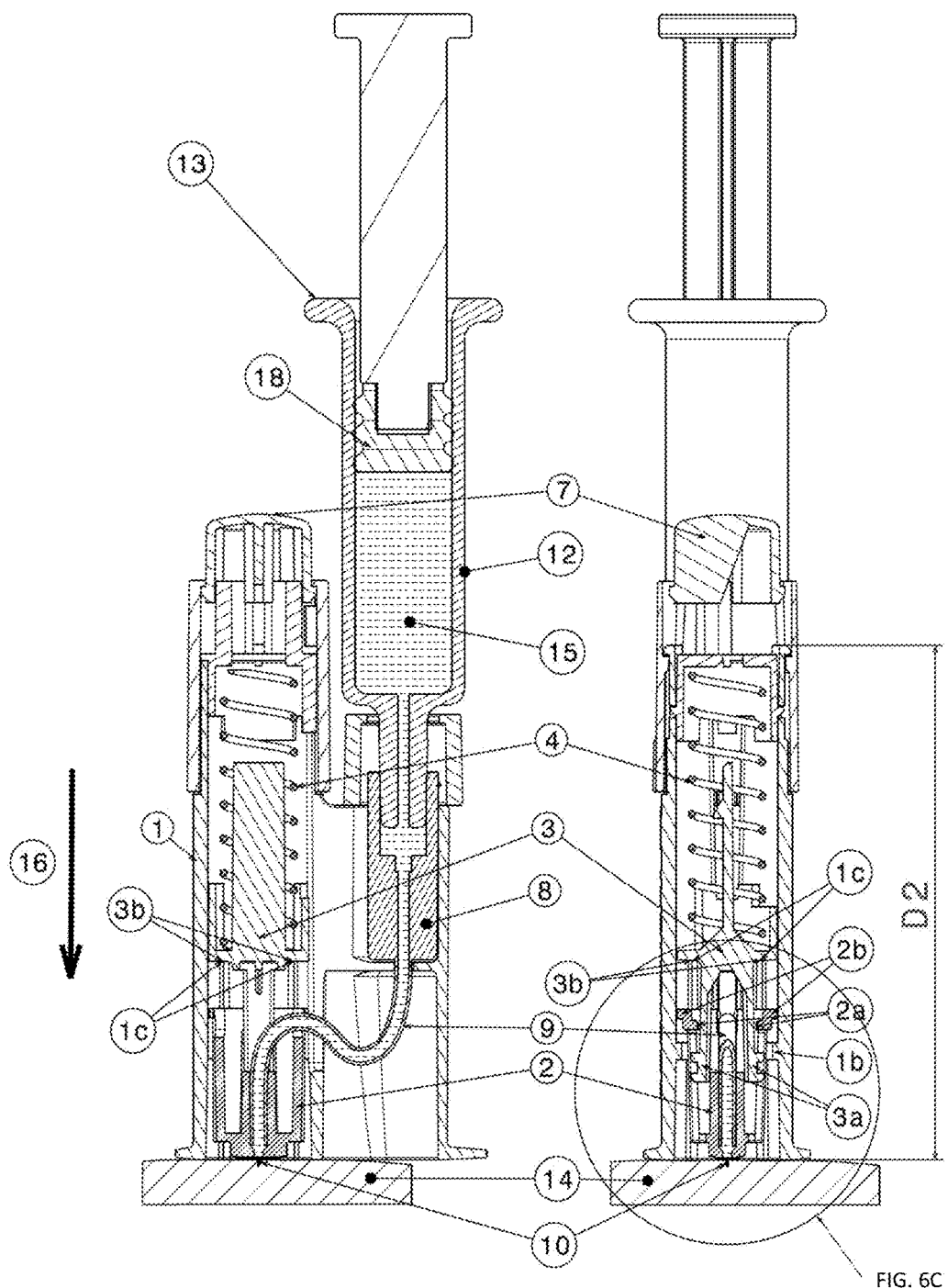
Figure 6C:
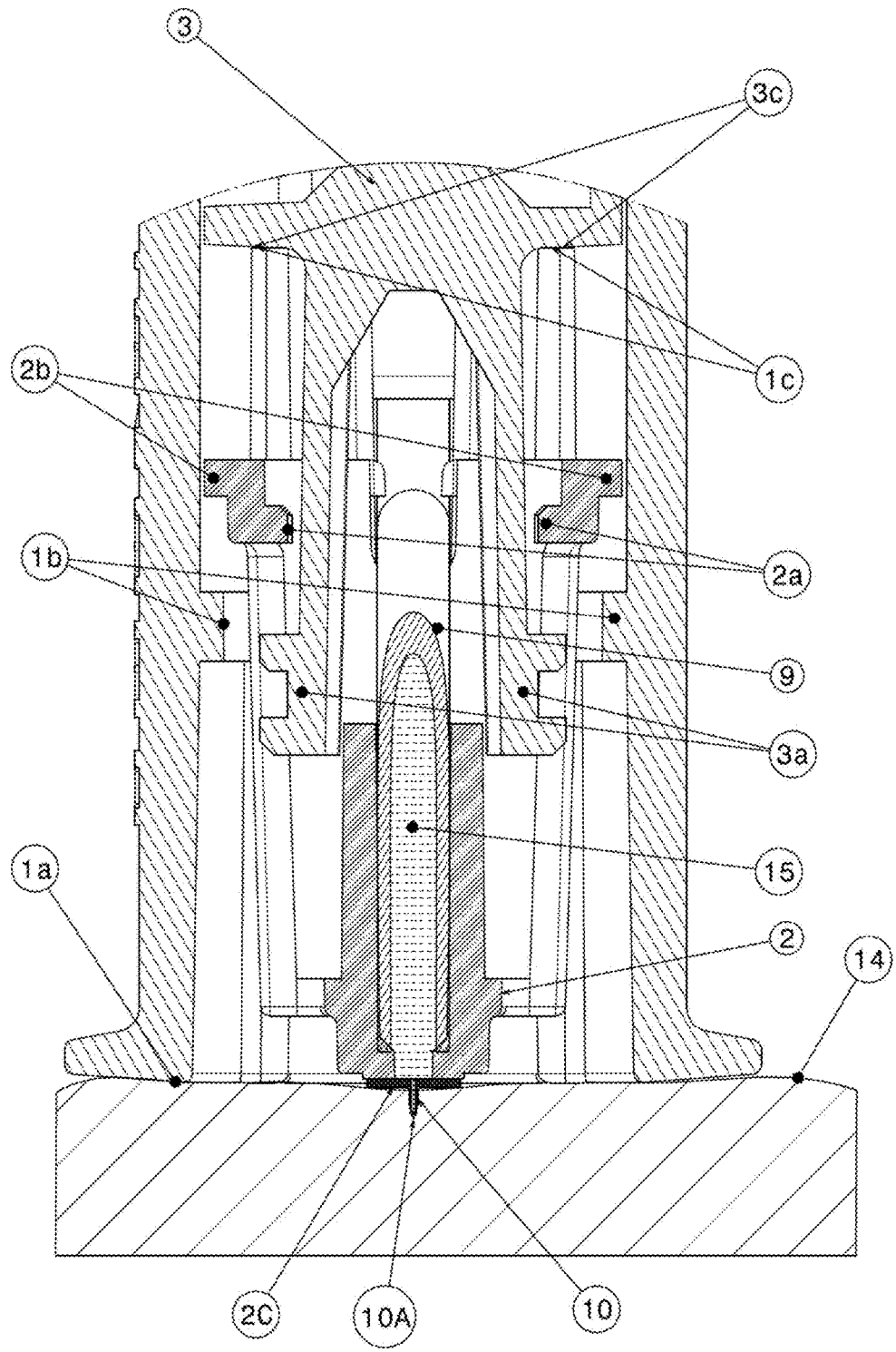

FIGS. 6a, 6b and 6c show the device with the plunger (2) in position 2, thus forming a distance D2 between the proximal end of the casing and the distal face (2a) of the plunger. This position normally corresponds to a return to equilibrium, where only the pressure means of the device exert a force in the direction of insertion (16).

Figures 7A, 7B:
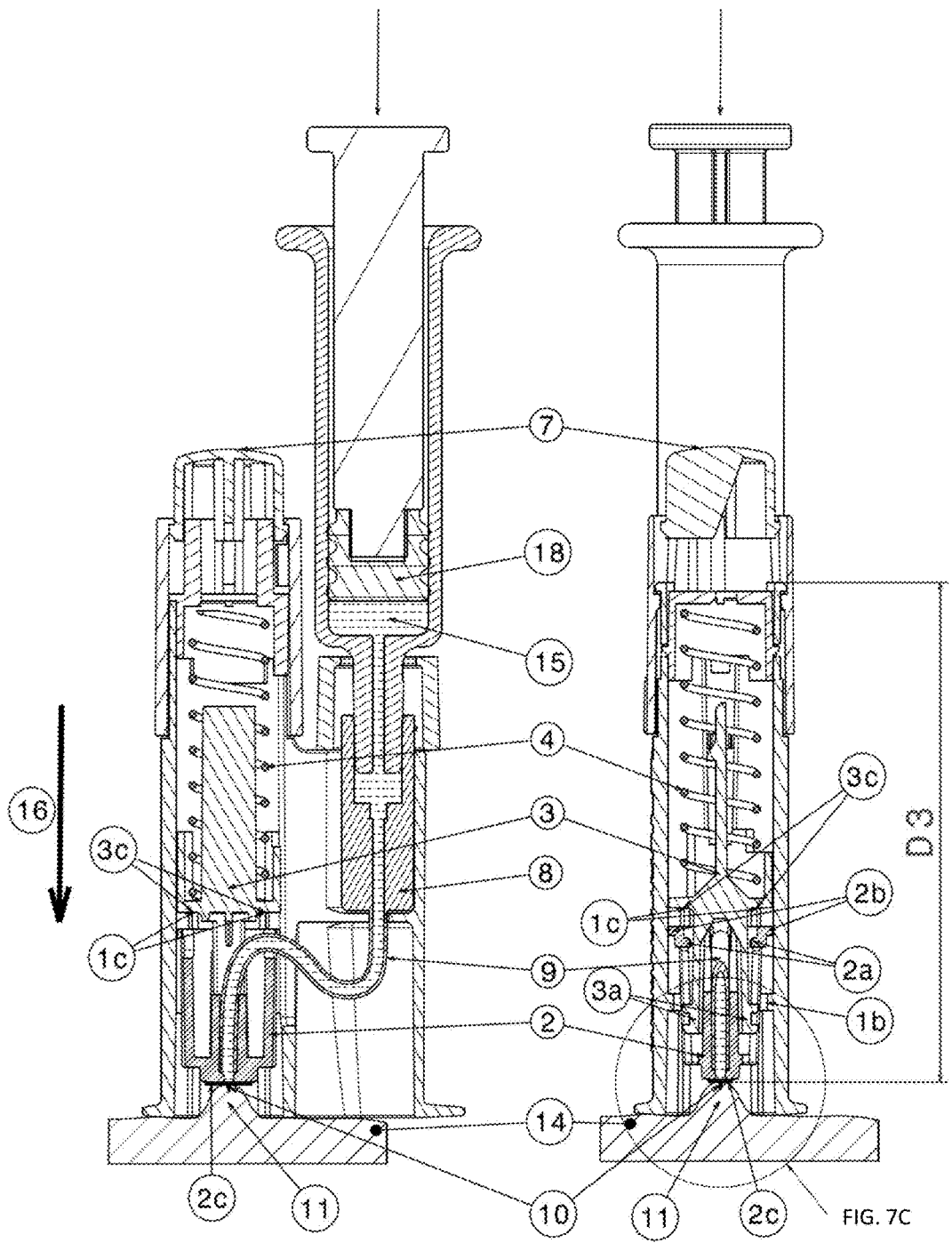
Figure 7C:
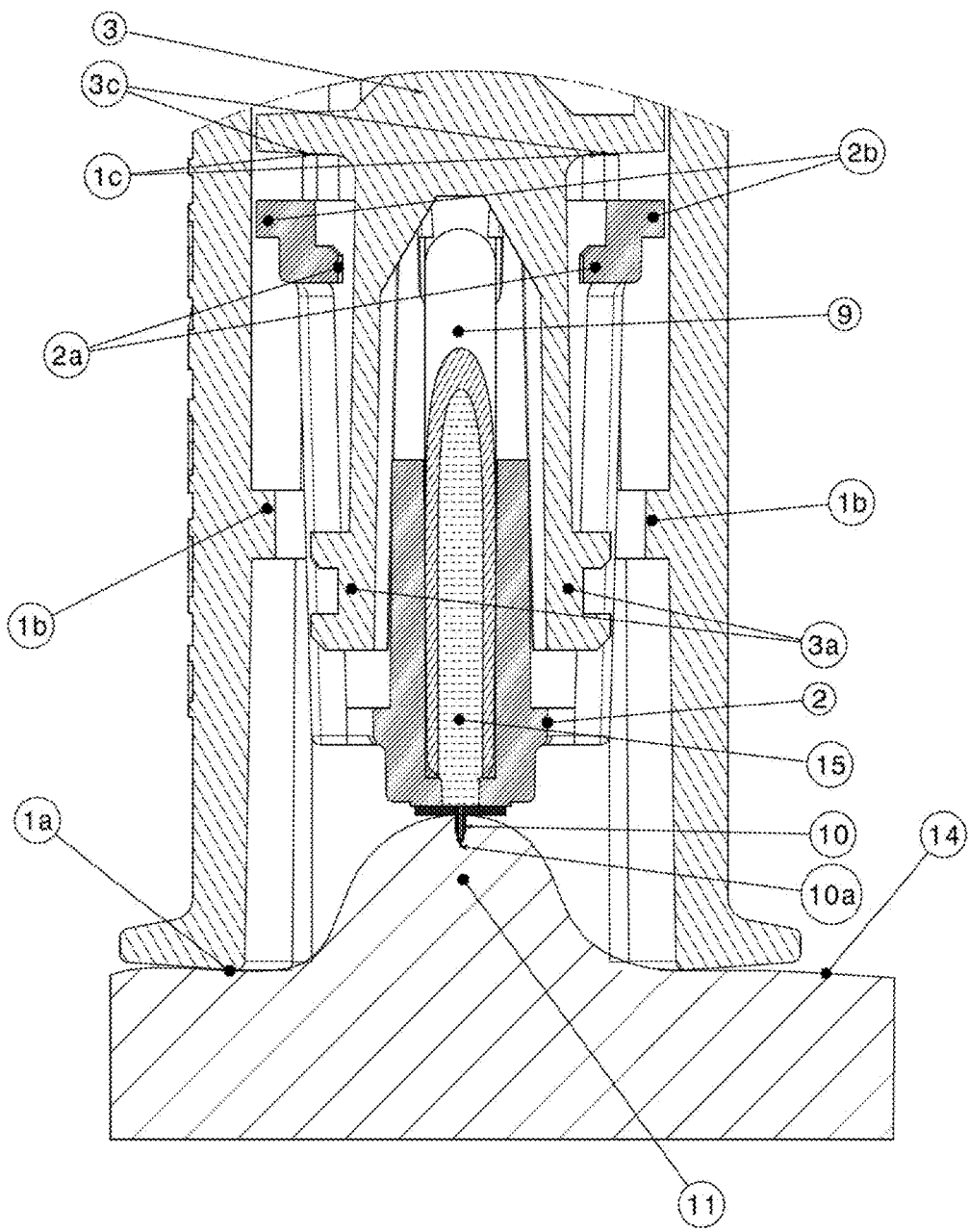

FIGS. 7a, 7b and 7c show the device with the plunger (2) in position 3, thus forming a distance D3 between the proximal end of the casing and the distal face (2a) of the plunger. This distance D3 is less than D1 and/or D2. At this stage, the operator applies a pressure to the plunger (18) of the syringe (13), injecting the solution (15) beneath the contact zone (17). The injection has the effect that an accumulation of the solution (15) under the contact zone (17) deforms the latter, thus forming a papule (11). The pressure means are configured to exert a minimum pressure so as not to oppose the formation of the papule (11). The needle/plunger assembly thus effects a return movement, which is controlled by the pressure means.

FIGS. 8 to 12 disclose the interaction between the plunger (2) and the thruster (3) from positioning to injection.

FIG. 8 shows the triggering of the plunger/thruster assembly rigidly connected by the retaining means (3a). The triggering of the thruster generates a force F1 exerted by the thrust means and drives the plunger (2) in the direction of the tissue.

FIG. 9 shows the needle which begins to penetrate the tissue. The plunger/thruster assembly is still rigidly connected and exerts a force F1 against the tissue. The mechanical characteristics of the tissue generate an oppositely directed force F2. The more the plunger advances against the tissue, the more the force F2 increases.

FIG. 10 shows the plunger in position 1. The needle has fully penetrated the tissue, and the force F2 has reached a predetermined value that allows the retaining means to unclip. To put it another way, the opposite directions of the forces F2 and F1 induce a radial force Fr, which is oriented in a direction perpendicular to the direction of the forces F1 and F2. The forces F1, F2 and Fr cause the thruster to slide inside the plunger and render the retaining means inoperative.

FIG. 11 shows the plunger in position 2, where F1 becomes zero because the plunger is disconnected from the thruster. A new force, called F3, is generated by the pressure means (4a). F3 is equal to F2, which corresponds to a state of equilibrium. The needle is inserted in the tissue, and the pressure means (4a) keep the needle correctly inserted.

FIG. 12 shows the plunger in position 3. The injection of the solution causes the formation of a papule. The pressure means exert a force F3 less than the force F4 generated by the formation of the papule. The force F3 makes it possible to keep the needle correctly inserted during the injection.

It goes without saying that the invention is not limited to the examples illustrated and to the embodiments disclosed in the present document.

REFERENCE NUMBERS USED IN THE FIGURES

1 Casing
1a Distal face of the device
1b Stop element for the plunger
1c Stop element for the thruster
1d Guide means
2 Plunger
2a Elements receiving the retaining means of the thruster
2b Retaining elements limiting the travel of the plunger
2c Distal face of the plunger
3 Thruster
3a Means retaining the thruster on the plunger
3b Retaining elements limiting the travel of the thruster
3c Means retaining the thruster on the casing
4 Spring of the thrust means
4a Spring of the pressure means
5 Element rigidly connected to the casing
6 Safety element of the trigger
7 Trigger
7a Triggering element
8 Luer
9 Tube
10 Needle
10a Distal end of the needle
11 Papule
12 Reservoir
13 Syringe
14 Tissue
15 Solution
16 Direction of insertion
17 Contact zone
18 Plunger of the syringe
19 Window
20 Drop

The invention claimed is:

1. A device for delivering a solution into or withdrawing a solution from a tissue of a patient, the device comprising:
   a thruster;
   a plunger having a proximal end and a distal end, the distal end configured to contact the tissue of the patient; and
   a needle protruding from the distal end of the plunger, wherein the plunger is attached to the thruster by a clip, wherein the clip is configured to
      (i) retain the plunger to the thruster so that the thruster can exert a first force on the plunger for inserting the needle into the tissue, and
      (ii) release the plunger from the thruster when an opposite force to the first force exerted by the thruster reaches a threshold such that the plunger can move relative to the thruster, the opposite force caused during the inserting of the needle.

2. The device according to claim 1, wherein a papule is formed in the tissue following the injection of the solution with the needle.

3. The device according to claim 1, wherein the pressure device and the clip are configured such that the first force and the second force are applied simultaneously to the tissue during a time period.

4. The device according to claim 1, further comprising:
   a pressure device mechanically connecting the plunger with the thruster, the pressure device configured to maintain a second force on the plunger in a same direction as the first force, after the plunger is released from the thruster by the clip, to keep the needle inserted in the tissue during an injection of the solution with the needle.

5. The device according to claim 4, wherein an intensity of the second force allows a slight retreat or movement of the needle with the tissue at a moment of forming a papule.

6. The device according to claim 4, wherein an intensity of the second force does not prevent a formation of a papule in the tissue induced by the injection of the solution.

7. The device according to claim 4, further comprising:
a receptacle for storing the solution, the receptacle being in fluidic connection with the needle, the receptacle configured to be actuated to administer the solution into the tissue via the needle.

8. The device according to claim 7, wherein the solution is administered via the needle when the pressure device applies the second force to the tissue.

9. A device for delivering a solution into or withdrawing a solution from a tissue of a patient, the device comprising:
propulsion means;
plunging means having a proximal end and a distal end, the distal end configured to contact the tissue of the patient; and
a needle protruding from the distal end of the plunging means,
wherein the plunging means is attached to the propulsion means by a retaining means,
wherein the retaining means
(i) retains the plunging means to the propulsion means so that the propulsion means can exert a first force on the plunging means for inserting the needle into the tissue, and
(ii) releases the plunging means from the propulsion means when an opposite force to the first force exerted by the propulsion means reaches a threshold such that the plunging means moves relative to the propulsion means, the opposite force caused during the inserting of the needle.

10. The device according to claim 9, wherein a papule is formed in the tissue following the injection of the solution with the needle.

11. The device according to claim 9, wherein the pressuring means and the retaining means are configured such that the first force and the second force are applied simultaneously to the tissue during a time period.

12. The device according to claim 9, further comprising:
pressuring means mechanically connecting the plunging means with the propulsion means, the pressuring means for maintaining a second force on the plunging means in a same direction as the first force, after the plunging means is released from the propulsion means by the clip, to keep the needle inserted in the tissue during an injection of the solution with the needle.

13. The device according to claim 12, wherein an intensity of the second force allows a slight retreat or movement of the needle with the tissue at a moment of forming a papule.

14. The device according to claim 12, wherein an intensity of the second force does not prevent a formation of a papule in the tissue induced by the injection of the solution.

15. The device according to claim 12, further comprising:
a receptacle for storing the solution, the receptacle being in fluidic connection with the needle, the receptacle configured to be actuated to administer the solution into the tissue via the needle.

16. The device according to claim 12, wherein the solution is administered via the needle when the pressuring means applies the second force to the tissue.

* * * * *